US008876790B2

(12) United States Patent
Rahimy et al.

(10) Patent No.: US 8,876,790 B2
(45) Date of Patent: Nov. 4, 2014

(54) CONNECTOR FOR CONTAINERS CONTAINING A MEDICINAL ACTIVE SUBSTANCE

(75) Inventors: Ismael Rahimy, Friedberg (DE); Torsten Brandenburger, Reichelsheim (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/574,304

(22) PCT Filed: Jan. 13, 2011

(86) PCT No.: PCT/EP2011/050376
§ 371 (c)(1),
(2), (4) Date: Aug. 28, 2012

(87) PCT Pub. No.: WO2011/092057
PCT Pub. Date: Aug. 4, 2011

(65) Prior Publication Data
US 2012/0313366 A1  Dec. 13, 2012

Related U.S. Application Data

(60) Provisional application No. 61/302,568, filed on Feb. 9, 2010.

(30) Foreign Application Priority Data

Jan. 26, 2010  (EP) .................................... 10151718

(51) Int. Cl.
*F16L 37/00*   (2006.01)
*A61J 1/00*    (2006.01)
(Continued)

(52) U.S. Cl.
CPC ............. *A61J 1/20* (2013.01); *A61M 2039/222* (2013.01); *A61M 39/10* (2013.01); *B65D*
(Continued)

(58) Field of Classification Search
CPC ................. A61J 1/10; A61J 1/12; A61J 1/20;
A61J 1/2089; A61J 1/1406; A61J 1/1475;
A61J 2001/2006; A61J 2001/201; A61J
2001/2027; A61J 1/14; A61M 39/221; A61M
2039/222; A61M 15/0031; A61M 39/14;
A61M 2039/221; A61M 2039/1061; A61M
39/10; Y10S 604/905; F16K 13/04; B65D
47/10; B65D 47/36; B65D 1/0238; B65D
2517/50; B65D 2517/5094
USPC .......... 604/411, 403, 407, 408, 412, 413, 414,
604/415, 416
See application file for complete search history.

(56) References Cited

U.S. PATENT DOCUMENTS
3,994,412 A * 11/1976 Difiglio ......................... 220/266
4,181,140 A *  1/1980 Bayham et al. ............. 137/68.28
(Continued)

FOREIGN PATENT DOCUMENTS
DE          88 12 460       12/1988
(Continued)

OTHER PUBLICATIONS
J.G.A. van Houten. "Large Strain Behaviour of Polycarbonate." Eindhoven University of Technology, Faculty of Mechanical Engineering, Department of Fundamentals of Mechanical Engineering. Report No. WFW 94.108. Eindhoven, Aug. 1994. http://alexandria.tue.nl/repository/books/653970.pdf.*

*Primary Examiner* — Adam Marcetich
(74) *Attorney, Agent, or Firm* — Occhiuti & Rohlicek LLP

(57) ABSTRACT

A connector according to the invention includes a first connection region for connecting a first container, a piercing element and a break-open element, wherein the piercing element has a first end section and a second end section and a channel, running from the first end section to the second end section, for transporting a medicinal active substance, wherein the first end section is formed for piercing a membrane of the first container connected in the first connection region, and, at the second end section, the break-open element is attached such that it can be broken open and/or broken off, wherein, in the attached state, the break-open element seals the channel of the piercing element in liquid tight fashion.

30 Claims, 6 Drawing Sheets

Figure 1:
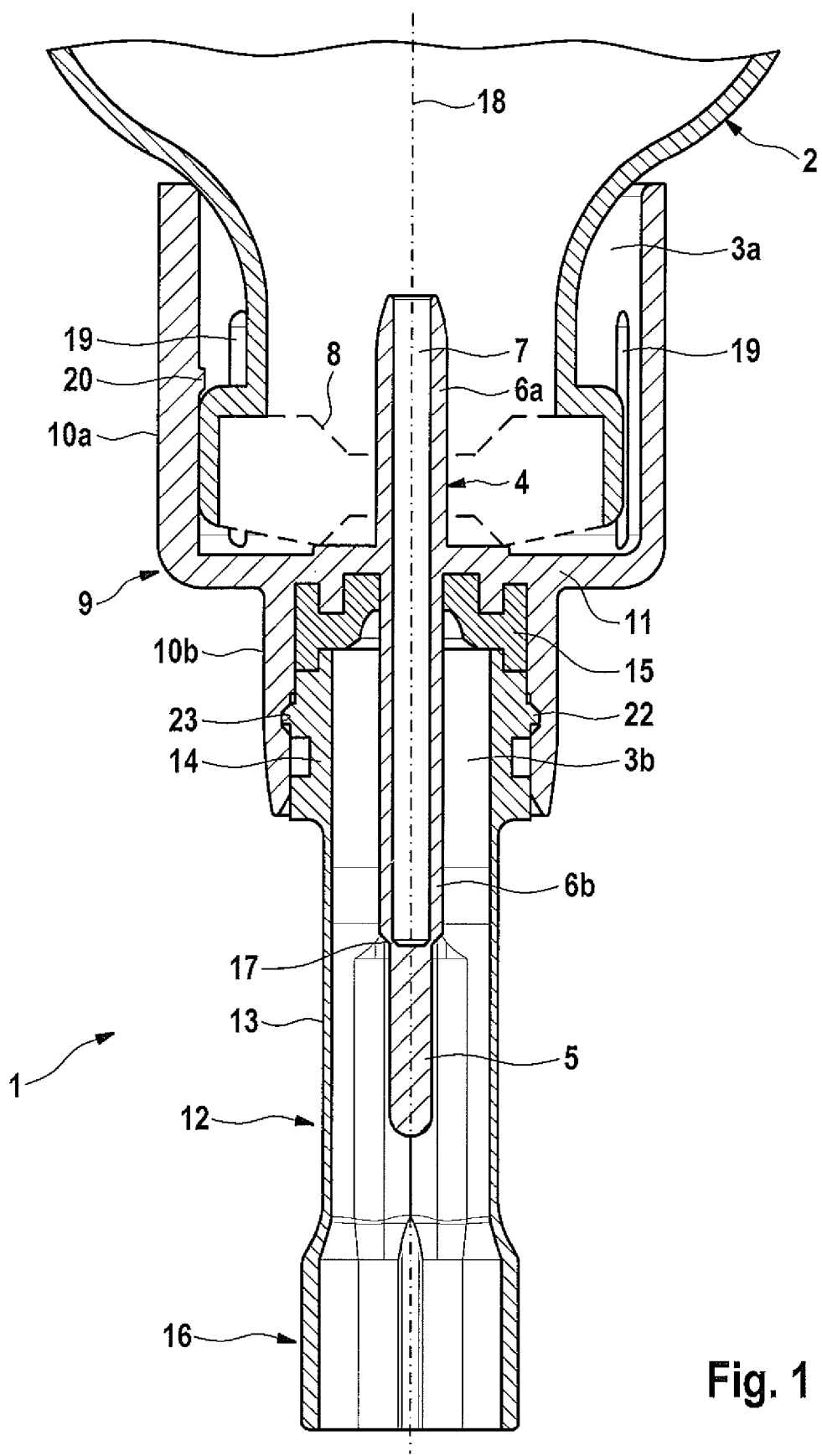

(51) Int. Cl.
*A61J 1/14* (2006.01)
*A61M 39/00* (2006.01)
*A61M 39/10* (2006.01)
*A61J 1/20* (2006.01)
*B65D 47/36* (2006.01)
*B65D 47/10* (2006.01)
*A61M 39/22* (2006.01)
*B65D 1/02* (2006.01)

(52) U.S. Cl.
CPC ..... 2517/50 (2013.01); *B65D 47/36* (2013.01); *A61J 2001/201* (2013.01); *A61J 2001/2027* (2013.01); *A61J 1/2089* (2013.01); *A61M 39/221* (2013.01); *B65D 1/0238* (2013.01); *B65D 47/10* (2013.01); *B65D 2517/5094* (2013.01)
USPC ........... 604/411; 604/403; 604/407; 604/408; 604/413; 604/414; 604/415; 604/416

(56) References Cited

U.S. PATENT DOCUMENTS

| | | | | |
|---|---|---|---|---|
| 4,402,682 A * | 9/1983 | Garver et al. | | 604/111 |
| 4,583,971 A * | 4/1986 | Bocquet et al. | | 604/82 |
| 4,588,402 A * | 5/1986 | Igari et al. | | 604/408 |
| 4,675,020 A * | 6/1987 | McPhee | | 604/411 |
| 4,911,696 A * | 3/1990 | Miyasaka et al. | | 604/244 |
| 5,152,755 A * | 10/1992 | Yoshinori | | 604/256 |
| 5,304,163 A * | 4/1994 | Bonnici et al. | | 604/403 |
| 5,330,464 A * | 7/1994 | Mathias et al. | | 604/415 |
| 5,372,590 A * | 12/1994 | Haber et al. | | 604/192 |
| 5,509,898 A * | 4/1996 | Isono et al. | | 604/87 |
| 5,662,642 A * | 9/1997 | Isono et al. | | 604/403 |
| 5,817,083 A * | 10/1998 | Shemesh et al. | | 604/416 |
| 6,132,413 A * | 10/2000 | Mathias et al. | | 604/403 |
| 2002/0193737 A1* | 12/2002 | Popovsky | | 604/110 |
| 2004/0116891 A1* | 6/2004 | Curutcharry | | 604/403 |
| 2004/0139968 A1* | 7/2004 | Loeffler et al. | | 128/200.24 |
| 2004/0199139 A1* | 10/2004 | Fowles et al. | | 604/414 |
| 2007/0244447 A1 | 10/2007 | Capitaine et al. | | |
| 2008/0015496 A1* | 1/2008 | Hamedi-Sangsari | | 604/87 |
| 2009/0120505 A1* | 5/2009 | Brierton et al. | | 137/68.11 |
| 2009/0198196 A1* | 8/2009 | West et al. | | 604/263 |
| 2009/0264854 A1* | 10/2009 | Jensen et al. | | 604/416 |
| 2010/0294693 A1* | 11/2010 | Lynn et al. | | 206/484 |

FOREIGN PATENT DOCUMENTS

| | | |
|---|---|---|
| EP | 0 624 358 | 11/1994 |
| EP | 1 859 773 | 11/2007 |
| WO | WO 87/02239 | 4/1987 |
| WO | WO 2007/149960 | 12/2007 |
| WO | WO 2009/130147 | 10/2009 |

* cited by examiner

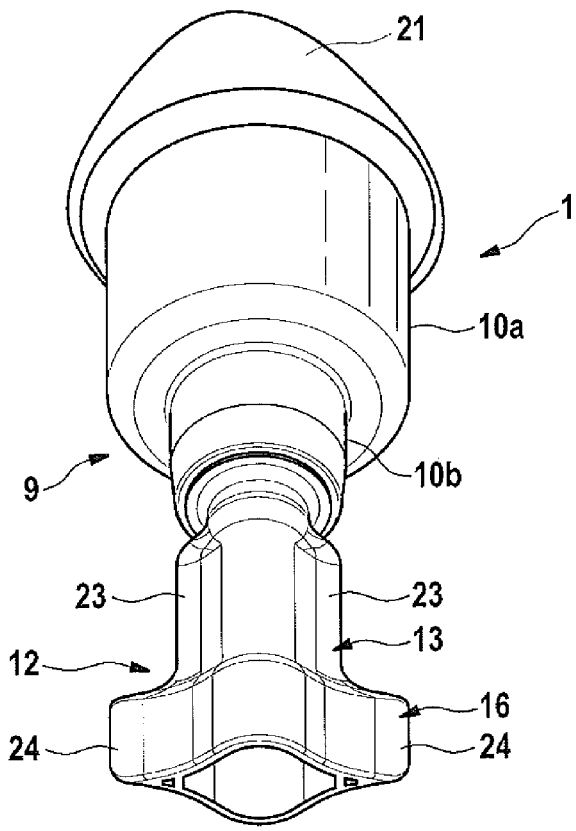
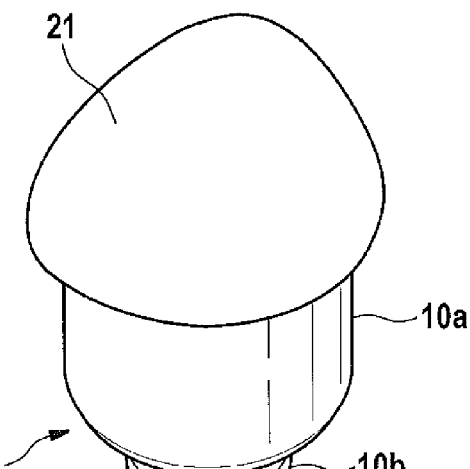
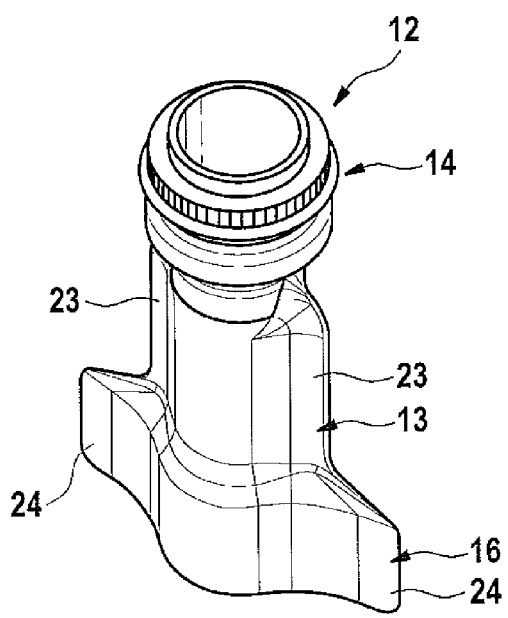
Fig. 2
Fig. 3
Fig. 4

CONNECTOR FOR CONTAINERS CONTAINING A MEDICINAL ACTIVE SUBSTANCE

CROSS REFERENCE TO RELATED APPLICATIONS

This application is the national phase of international application no. PCT/EP2011/050376, filed Jan. 26, 2011, which claims priority to European application no. 10151718.3, filed Jan. 26, 2010, and U.S. provisional application No. 61/302,568, filed Feb. 9, 2010. The contents of the aforementioned applications are incorporated herein in their entirety.

DESCRIPTION

Technical Field

The invention relates to a connector for containers containing a medicinal active substance, making it possible to transfer an active substance from one container into another container.

PRIOR ART

EP 1 066 812 A2 discloses a connector for containers containing a medicinal active substance, having a first connection region for connecting a glass vial, a second connection region for connecting a flexible bag and a piercing element. The piercing element is embodied in the form of a two-sided cannula. The first and the second connection region are formed by a common housing. The housing can be detachably connected to a connection means in the second connection region, wherein the connection means is connected to the flexible bag. The connection means comprises a membrane, which seals the access to the bag in liquid tight fashion. As a result of connecting the glass vial to the housing in the first connection region, the piercing element pierces a rubber plug provided in the cover of the glass vial. As a result of connecting the connection means to the housing of the connector, the piercing means also pierces the membrane arranged in the connection means. As a result of piercing the membrane of both the glass vial and the membrane of the connection means, the piercing element can be used to transfer an active substance situated in one of the containers into the other container.

BRIEF DESCRIPTION OF THE INVENTION

The connector according to the invention for containers containing a medicinal active substance comprises a first connection region for connecting a first container, a piercing element and a break-open element, wherein the piercing element has a first end section and a second end section and a channel, running from the first end section to the second end section, for transporting a medicinal active substance, wherein the first end section is formed for piercing a membrane of a first container connected in the first connection region, and, at the second end section, the break-open element is attached such that it can be broken open and/or broken off, wherein, in the attached state, the break-open element seals the channel of the piercing element in liquid-tight fashion.

In the attached state, the break-open element keeps the channel of the piercing element sealed such that no active substance from the container can yet be taken from a container, which container is completely connected to the first connection region of the connector, or no active substance can yet be transferred thereto. Transportation of the active substance through the piercing element is only made possible by breaking open and/or breaking off the break-open element. Breaking open and/or breaking off the break-open element enables quick, safe and sterile opening of the channel from the outside without the risk of injury or damage to the user or the container to be connected, in contrast to, for example, piercing a membrane with a cannula. As a result of attaching the break-open element at the end section of the piercing element, the connector can be embodied in a compact fashion and additional elements which hold the break-open element in its position can be dispensed with.

The containers, which can be connected or attached by the connector, can be both closed containers, for example glass flasks, plastic flasks or bags, more particularly flexible bags, or "open" containers, for example catheters or other lines, as are used in, for example, infusion, transfusion, clinical feeding, oncology, dialysis or other medical fields. The medicinal active substance which can be transferred from one container to the other by means of the connector can for example be a liquid or a powder.

The predetermined breaking point at which the break-open part is broken off is preferably designed such that the break-open part is merely partly broken off, i.e. broken open, by a break-open movement such that, although the active substance can pass through the channel, the break-open part remains connected to the piercing element and hence is unable to enter a container. Moreover, the connector is embodied such that the break-open part can preferably be broken open with one hand by using thumb and index finger. In an alternative variant, the predetermined breaking point is designed for the break-open element to break off completely. Complete breaking off of the break-open element can also take place after the latter has broken open.

In an advantageous embodiment of the invention, the piercing element and the break-open element have an integral design, preferably as injection molded part. This enables a cost-effective production of the connector. As an alternative, it would for example likewise be possible for piercing element and break-open element to have a multipart design and for the break-open element to be connected to the piercing element in liquid-tight fashion, for example by means of a material bond or other suitable connection techniques, e.g. welding or adhesive bonding.

In a further advantageous embodiment, the connector comprises a housing with a first housing section, forming the first connection region, and a housing base, wherein the piercing element passes through the housing base.

Housing, piercing element and break-open element preferably have an integral design, for example as injection molded part. Moreover, it is preferable to produce piercing element, break-open element and, optionally, housing from a plastic, in particular from a polypropylene, polycarbonate and/or a blend, preferably a blend of polycarbonate and styrene-ethylene/butylene-styrene block copolymer (SEBS).

Further advantageous embodiments are described in the dependent claims.

The invention will be described in more detail in the following text on the basis of exemplary embodiments, which are illustrated by a number of figures.

BRIEF DESCRIPTION OF THE FIGURES IN THE DRAWING

Figure 5:
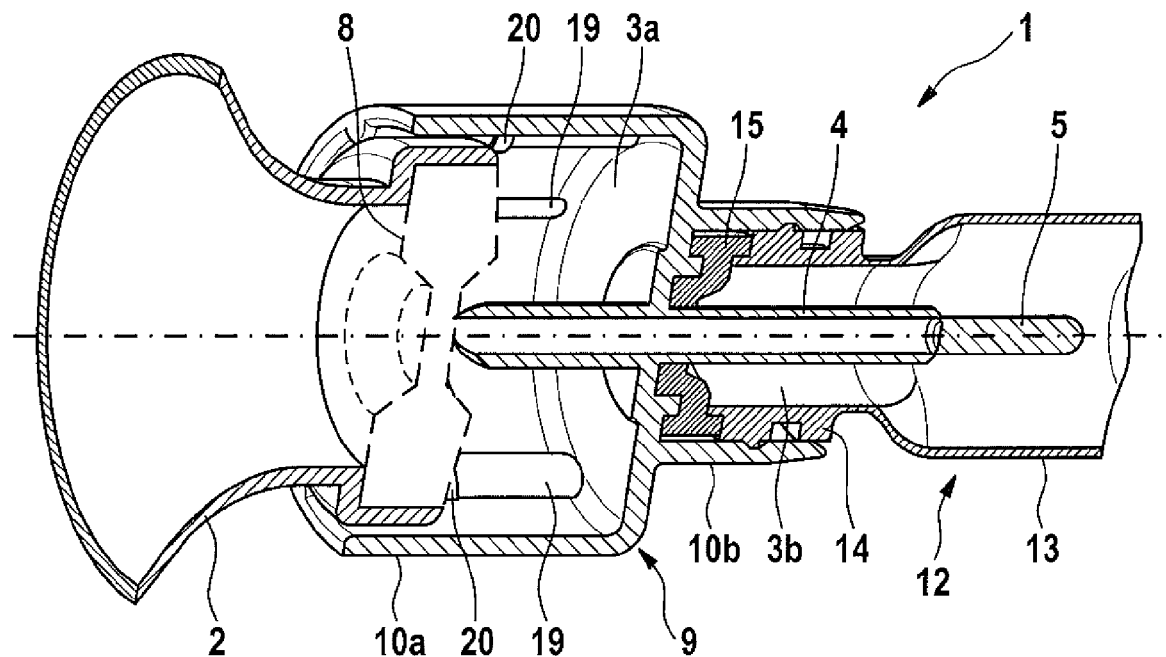
Figure 6:
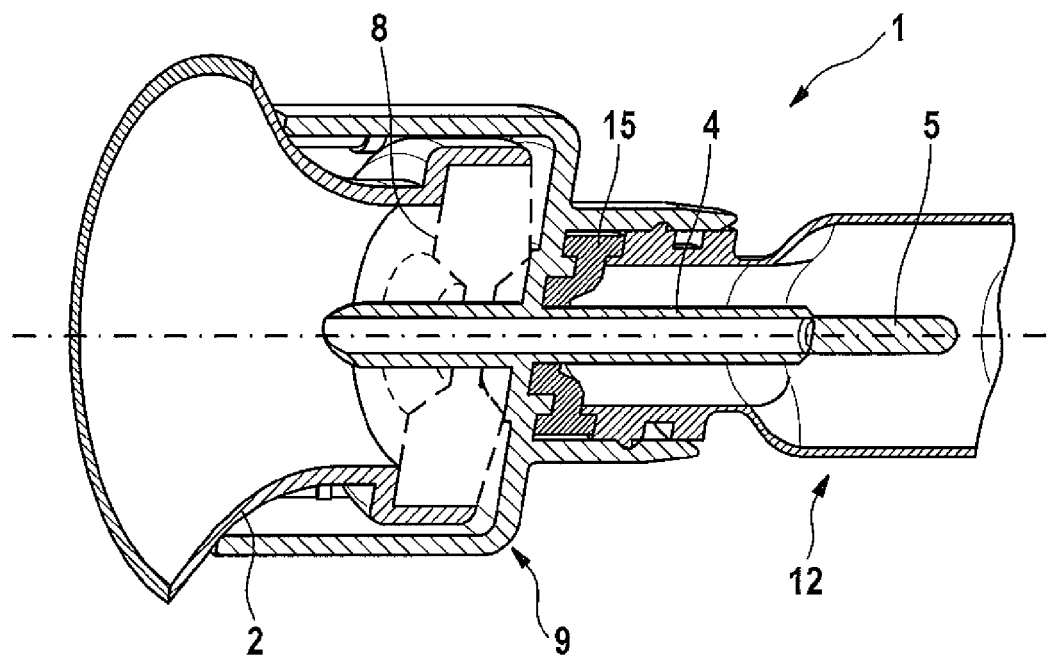
Figure 7:
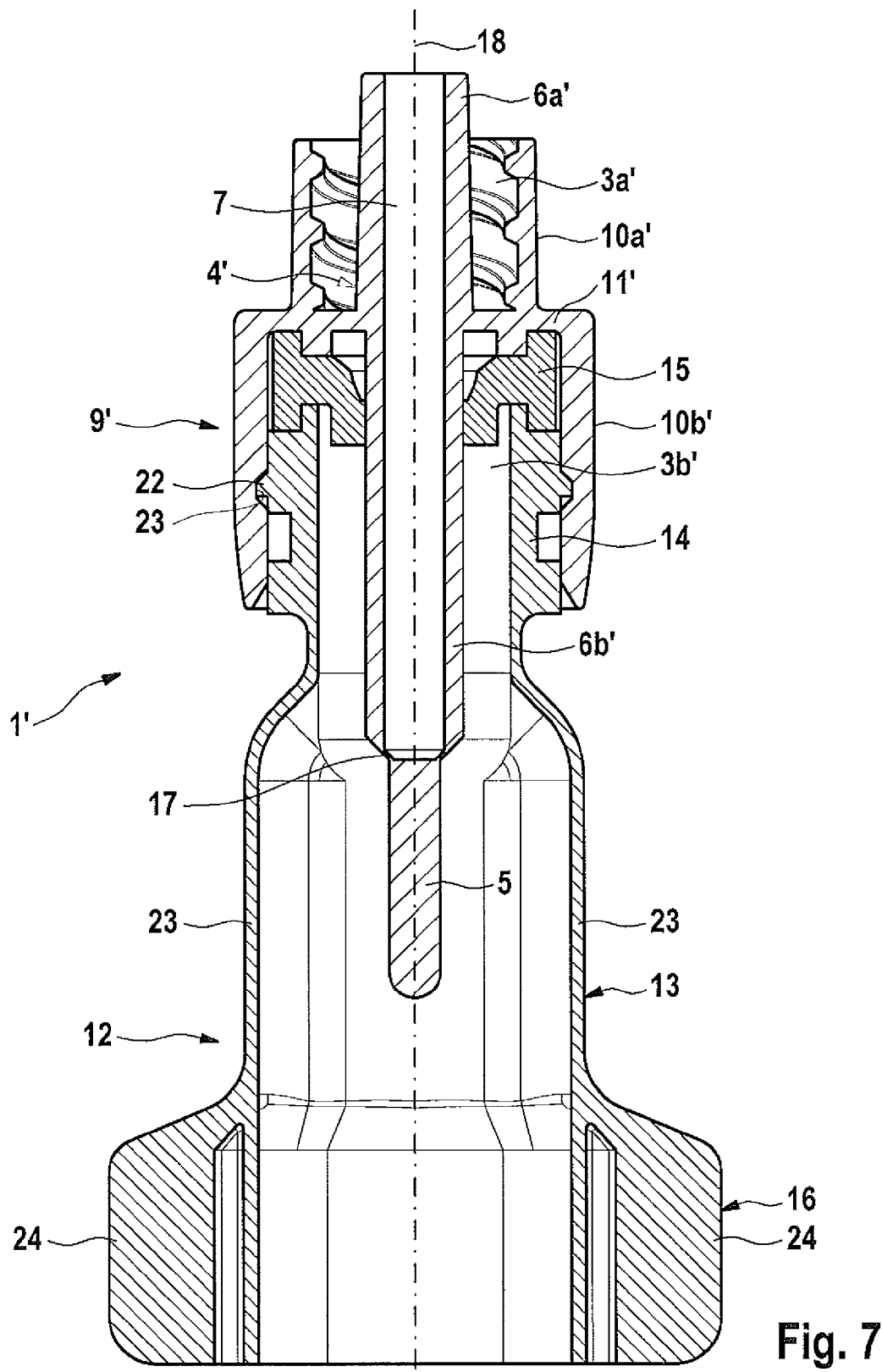
Figure 8:
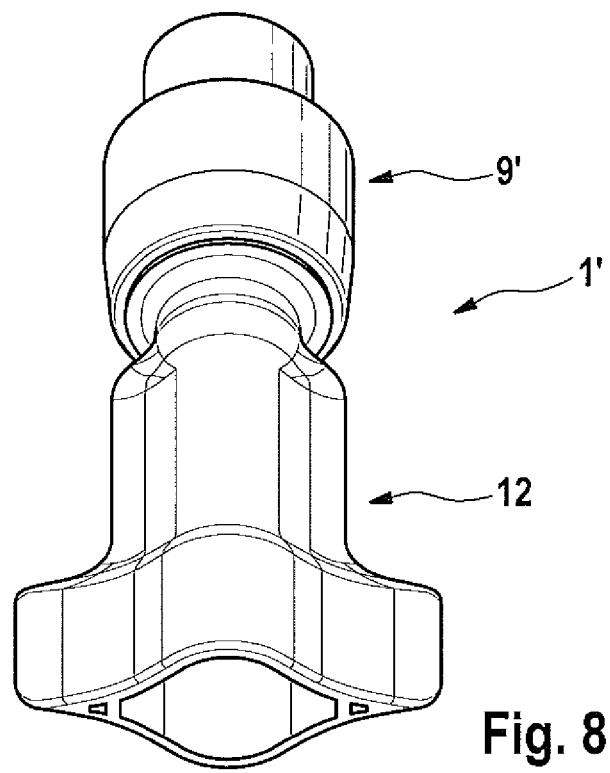
Figure 9:
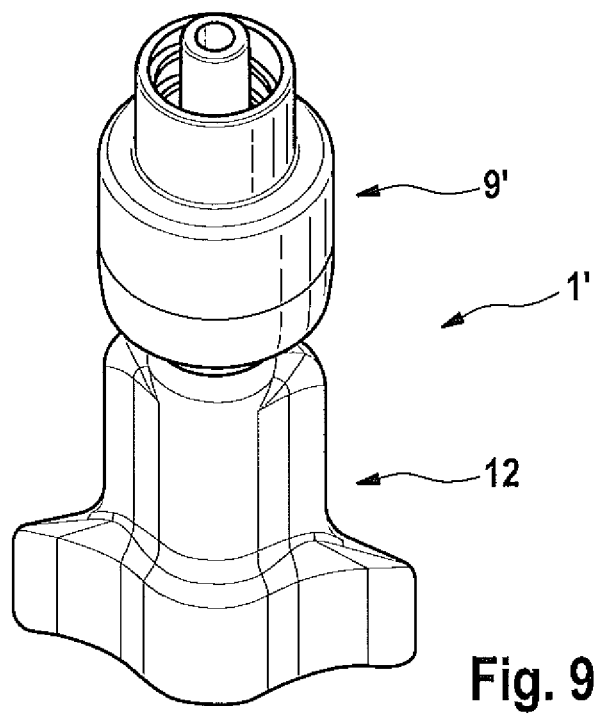
Figure 10:
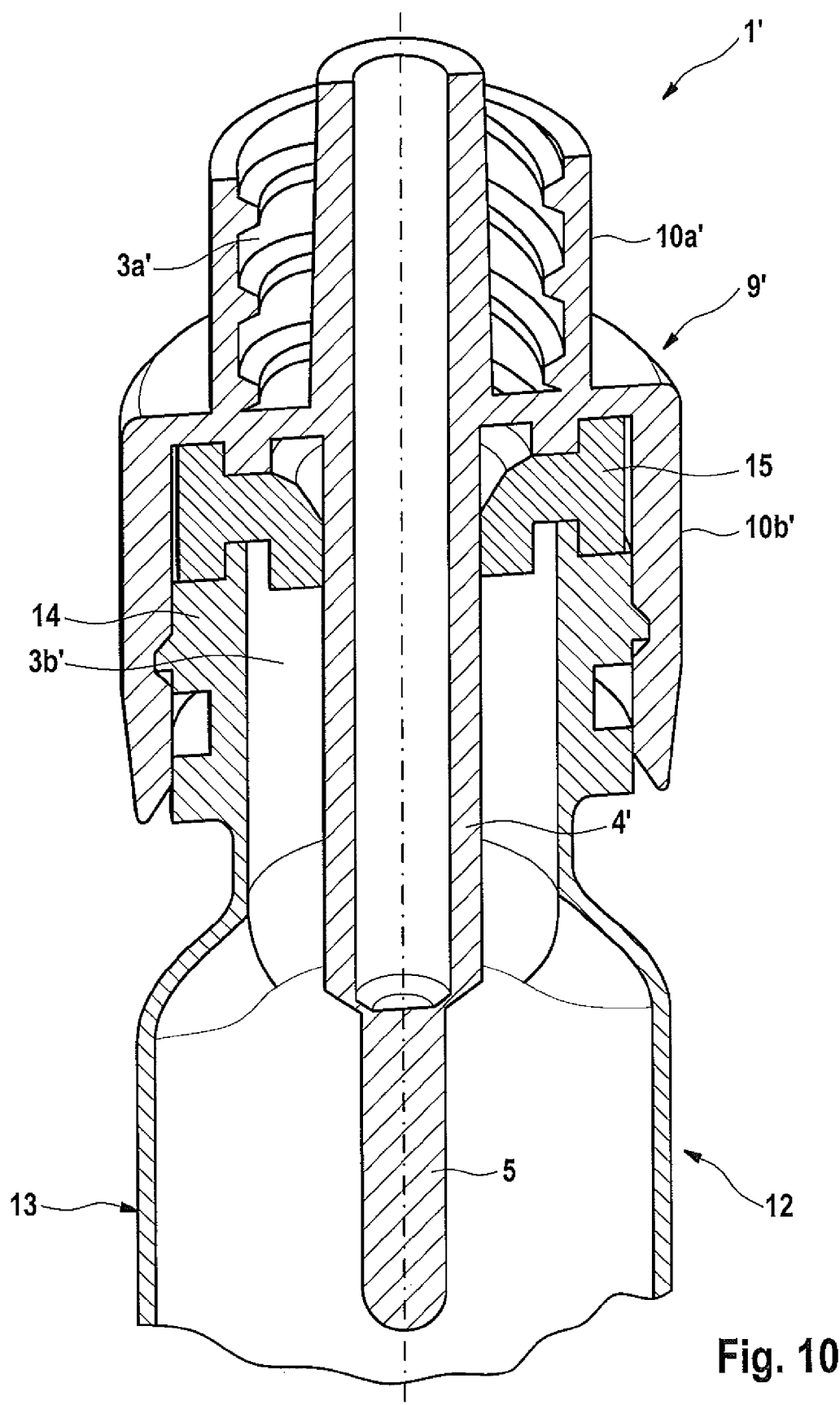

In detail:

FIG. 1 shows a longitudinal section through a first embodiment of a connector according to the invention, FIG. 2 shows a first perspective view of the connector shown in FIG. 1, FIG. 3 shows a further perspective view of the connector shown in FIG. 1, FIG. 4 shows a perspective view of the connection means of the connector shown in FIG. 1, FIG. 5 shows a view of the connector, cut open along the longitudinal axis, with a glass flask connected in a docking position, FIG. 6 shows a view of the connector, cut open along the longitudinal axis, with a glass flask connected in an end position, FIG. 7 shows a longitudinal section through a second embodiment of a connector according to the invention with a Luer lock connection, FIG. 8 shows a first perspective view of the connector shown in FIG. 7, FIG. 9 shows a further perspective view of the connector shown in FIG. 7 and FIG. 10 shows a view of the connector shown in FIG. 7, cut open along the longitudinal axis.

DESCRIPTION OF THE EMBODIMENT TYPES

FIGS. 1 to 6 show various views of a first embodiment of a connector 1 according to the invention for containers containing a medicinal active substance.

The connector 1 comprises a first connection region 3a for connecting a first container, a second connection region 3b for connecting a second container, a piercing element 4 and a break-open element 5. Moreover, the connector 1 comprises a housing 9 with a first housing section 10a, a second housing section 10b and a housing base 11, wherein the first housing section 10a forms the first connection region 3a and the second housing section 10b forms the second connection region 3b. The piercing element 4 passes through the housing base 11. The housing 9, the piercing element 4 and the break-open element 5 are designed in a substantially rotationally symmetric fashion about a common axis of symmetry 18.

The piercing element 4 is embodied in the form of a tubule. The piercing element 4 comprises a first end section 6a, which in this case extends into the connection region 3a, and a second end section 6b, which in this case is situated over the second connection region 3b. The inner hollow space of the piercing element 4 forms a channel 7, running from the first end section 6a to the second end section 6b, for transporting a medicinal active substance. The first end section 6a is designed for piercing a membrane of a container connected in the first connection region 3a, for example for piercing a rubber plug 8 (indicated by a dashed line) of a glass vial 2. In order to simplify the piercing, the end of the end section 6a is formed with a sharp tip, preferably beveled or sharpened, for example in the form of a cannula. At the second end section 6b, the break-open element 5 is attached directly to the tip of the piercing element 4 in such a manner that it can be broken open by hand, wherein, in the attached state, the break-open element 5 seals the channel 7 of the piercing element 4 in liquid-tight fashion. A connection area 17 between break-open element 5 and piercing element 4 is embodied such that the channel 7 is opened by snapping-back the break open element 5 with respect to the piercing element 4, but the connection between the break-open element 5 and the piercing element 4 is partly maintained such that the break-open element 5 does not detach from the piercing element 4. In this exemplary embodiment, the connection area 17 is embodied as radially encircling web, which connects the tip of the end section 6b with the opposing end of the break-open element 5. The break-open element 5 is embodied in the form of a pin, which, in the attached state, adjoins the piercing element 4 in an axial and undercut-free manner.

Alternatively, the connection area 17 can be embodied such that the break-open element 5 can be completely broken off by a snapping-back movement. In a further variant, the break-open element 5 can be broken off by breaking open being followed by breaking off, for example as a result of two opposing bending movements.

The first housing section 10a and the second housing section 10b substantially have a hollow-cylindrical or tubular design. The outer radius of the first housing section 10a, which in this case is embodied for holding a glass vial 2, is greater than the outer radius of the second housing section 10b. The housing base 11 is situated between the first housing section 10a and the second housing section 10b and, on the respective side, forms the base of the first connection region 3a and of the second connection region 3b. The first housing section 10a comprises a plurality of clamping webs 19, running in the axial direction, the purpose of which during the insertion of the container 2 into the connection region 3a is to already prefix, by clamping, said container in a docking position in which the piercing element 4 has not yet pierced the membrane 8 (see FIG. 5) and more particularly to prevent undesired slipping-out of the container, for example as a result of the gravitational force. Projections 20 are provided on the clamping webs 19 at a common height, the former forming an undercut and having the purpose of additionally holding the container 2 by means of interlocking fit in a completely inserted state of the container 2, in which the piercing element 4 has pierced the membrane 8 (see also FIG. 6).

A further undercut can be provided in the connection region 3a, for example by additional projections, said undercut already fixing the container 2 in the docking position by forming an interlocking fit. The clamping webs 19 can likewise be present in this variant; however, alternatively, these can also be dispensed with. Such a second undercut makes it easier to connect containers with different dimensions to the connector 1.

In this exemplary embodiment, housing 9, piercing element 4 and break-open element 5 are embodied in integral fashion as an injection molded part. A preferable material is a thermoplastic plastic, preferably a polypropylene, polycarbonate and/or a blend, preferably a blend of polycarbonate and styrene-ethylene/butylene-styrene block copolymer. Moreover, it is preferably to use a hard plastic. This ensures a suitable stiffness of this part.

In this exemplary embodiment, the connector 1 additionally has a cover film 21 which can be pulled-off by hand (see FIG. 2 and FIG. 3), for example an aluminum or plastic film, which covers the first connection region 3a for protecting the first connection region 3a against contamination. Such a cover film 21 is optional; the connector 1 can be designed without it.

The connector 1 furthermore comprises a connection means 12 formed for transporting the medicinal active substance. The connection means 12 comprises a manually elastically deformable bending section 13, a connection section 14 and a weld section 16. The connection means 12 is connected to the housing 9 by means of a snap-in connection on the second housing section 10b via the connection section 14 in the second connection region 3b. The connection means 12 is embodied as hollow body and surrounds the second end section 6b and the break-open element 5. The break-open element 5 is at least partly situated in the elastically deformable bending section 13 such that the break-open element 5 can be broken open by snapping the bending section 13 once.

The connection section 14 comprises an attachment web 22, which is on the outer surface in a radially encircling manner and latched into a groove 23, corresponding thereto, on the inner surface of the second housing section 10b by inserting the connection section 14 into the second housing section 10b. The connection means 12 is fixed to the housing 9 by this interlocking fit formed thus. The connector 1 comprises a sealing means 15, in this case a sealing membrane made of silicone or polyisoprene, which is arranged between housing 9 and connection means 12 on the base of the second connection region 3b and which seals the connection means 12 against the housing 9 in liquid-tight fashion such that the active substance cannot escape in the connection region between housing 9 and connection means 12 when transporting a medicinal active substance through the piercing element 4 and the connection means 12. The sealing means 15 ensures that there is a sufficient seal, even if different materials are used for connection means 12 and housing 9, even in the case of temperature variations, for example. Moreover, tolerance variations can also be taken into account. The sealing means 15 is held in a clamping manner between the connection means 12 and the housing 9 by elastic deformation of the sealing means 15.

The bending section 13 comprises two stiffening webs 23, which are situated on the outside, run in the axial direction and have a mirror symmetric design, see FIGS. 2, 3. The stiffening webs 23 on the one hand bring about a stiffening of the connection means 12 in the bending section 13, on the other hand the stiffening webs 23 set a defined snapping direction, in which the connection means 12 can be snapped-back in the bending section 13 and hence the break-open element 5 can be broken open.

The weld section 16 comprises two wing-shaped weld tabs 24 with a mirror-symmetric design, which tabs, in this case, are designed as a continuation of the stiffening webs 23. The weld tabs are particularly suitable for connecting the connection means 12 to a flexible bag (not illustrated here in any more detail) in liquid-tight fashion.

The connection means 12 has an integral design made of plastic. A plastic which is flexible relative to the material of the housing 9 is preferable, preferably a thermoplastic plastic, for example a polypropylene or a polypropylene-SEBS blend which can be welded to the material of the respective container, in this case the bag. A flexible plastic enables the formation of the manually elastically deformable bending section 13. Connection section 14 and weld section 16 have a thicker wall strength and/or stiffenings compared to the bending section 13, as a result of which the former two sections are relatively dimensionally stable, which is advantageous for a secure connection of the connection means 12 to the housing 9 and to the bag or another container.

In order to connect a container to the connector 1, the cover film 21 is first of all removed. The container, for example the container 2 embodied as a glass vial, is subsequently inserted into the first connection region 3a until said container encounters the projections 20 ("docking position"), see FIG. 2. The container 2 is prefixed in this position, but the membrane 8 of the container 2 has not yet been pierced, and so the container 2 can be re-separated from the connector 1 without opening the container 2. During the further insertion of the container 2, the membrane 8 is pierced by the piercing element 4 and the container 2 is fixed in an interlocking manner on the connector 1 by the projections 20 ("end position"), see FIG. 6. By bending/snapping the connection means 12 in the bending section 13, the break-open element 5 can now be broken open and the channel 7 can be opened thereby, as a result of which transport of an active substance, for example a liquid, is made possible between a container connected by the connection means 12 or mixing of a powder with the contents of a container, more particularly a flexible bag, connected to the connection means 12 and the container 2 is made possible. Bending or snapping the connection means 12 can more particularly be brought about with one hand by using thumb and index finger.

The container 2 can be preassembled on the connector 1 in the docking position. Container 2, connector 1 and a second container, more particularly a bag, connected to the connector 1 can be additionally enclosed in a further bag as a set. The enables the quick mixing, transferring, dissolving or thinning of an active substance, without there being a danger of the active substance undesirably escaping to the outside.

FIGS. 7 to 10 show a second embodiment of a connector 1' according to the invention.

According to the second embodiment, the first connection region 3a' and, accordingly, the first housing section 10a' and the housing base 11 are embodied as male part of a Luer lock (ISO 594/1-1986). The connection means 12, the sealing means 15 and the second housing section 10b correspond to the respective elements of the first embodiment of the connector 1; reference in this respect is made to the explanations relating to the first embodiment. The piercing element 4' is embodied according to the requirements of the male part of the Luer lock in its section lying on the side of the first connection region 3a', more particularly in the end section 6a'; the part lying on the side of the second connection region 3b corresponds to the part of the first embodiment of the connector 1. As a result, a container with a Luer female part can be connected to the connector 1' in the first connection region 3a'. The female part can have a membrane which can be opened by the end section 6a'. Or, alternatively, the female part can also be embodied without a membrane.

The breaking open is brought about in both embodiments by simple snapping back in the radial direction to the connection area 17. To this end, the break-open element 5 can be held indirectly via the elastic bending section 13 by thumb and index finger and the connector 1, 1' can subsequently be snapped back relative to the bending section 13 by the other hand in the region facing away from the connection area 17, for example on the housing 9, 9'. As a result of a one-sided snapping movement, the connection area 17 is detached on the side facing away from the snapping movement; part of the connection area 17 remains in standing on the other side and forms a hinge for the further snapping movement. The hinge connects the break-open element 5 with the piercing element 4, and so the break-open element 5 remains connected to the piercing element 4, even in the case of liquid transport through the piercing element 4. As a result of a second snapping movement, more particularly in the opposite direction, it is possible to completely break off the break-open element 5.

In terms of materials, the materials utilized for the piercing element 4 and the break-open element 5 can be used, for example polyolefins or polycarbonate. In the case of containers which are not steam-sterilizable, it is also possible to use ABS, polystyrene and comparable materials. In principle, the material of the connection area 17 can differ from the materials of the piercing element 4 and/or the break-open element 5.

The wall strength of the connection area 17 depends on the utilized materials. It is preferably in a range between 0.1 mm and 0.3 mm. Moreover, it is possible to design the connection area with a reduced wall strength in an angular range, for example in an angular range greater than 180° or in an angular range greater than 250°, for example approximately 270°, compared to the remaining angular range, as a result of which a hinge region and a break-open region can be defined. The break open region and the hinge region can have an optically different design in order to indicate the snapping direction to the user.

The connector 1, 1' according to the invention can be produced in a cost-effective manner from a small number of parts, enables the secure connection between two containers without the risk of damaging a container or injuring the user, and makes it possible to open, by means of a simple movement that can be carried out by hand, the connection between the two containers for transferring an active substance. Moreover, in principle, the connector is suitable for connection to any containers, e.g. also for connection to syringes or catheters, with an appropriate design of the first connection region 3a, 3a' and of the connection means 12.

The invention claimed is:

1. A connector for containers containing a medicinal active substance, comprising
   a first connection region for connecting a first container,
   a piercing element and a break-open element,
   wherein the piercing element has a first end section and a second end section and a channel, running from the first end section to the second end section, for transporting the medicinal active substance,
   wherein the first end section is formed for piercing a membrane of a first container connected in the first connection region, and, at the second end section, the break-open element is attached such that it can be broken open via a connection area, and
   wherein, in the attached state, the break-open element seals the channel of the piercing element in liquid-tight fashion, and
   a connection with a manually elastically deformable bending section, wherein the connection surrounds the second end section and the break-open element is at least partly situated in the bending section such that the break-open element can be broken open as a result of a deformation of the bending section, the bending section including two stiffening webs positioned in the bending section, wherein the two stiffening webs provide a stiffening of the connection in the bending section and define a snapping direction of the bending section
   wherein the two stiffening webs lie in a plane and the snapping direction is transverse to the plane.

2. The connector as claimed in claim 1, wherein the break-open element is configured to be completely broken off by a further snapping movement.

3. The connector as claimed in claim 1, wherein the piercing element is integrally formed with the break-open element.

4. The connector as claimed in claim 1, wherein the break-open element adjoins the piercing element in an undercut-free manner.

5. The connector as claimed in claim 1, wherein the piercing element and the break-open element are made of plastic.

6. The connector as claimed in claim 5, wherein the piercing element and the break-open element are made of polypropylene and/or of polycarbonate and/or of a blend and/or of a blend of polycarbonate and styrene-ethylene/butylene-styrene block copolymer.

7. The connector as claimed in claim 1, additionally comprising a housing with a first housing section, forming the first connection region, and a housing base, wherein the piercing element passes through the housing base.

8. The connector as claimed in claim 7, additionally comprising a second connection region for connecting a second container wherein the housing has a second housing section of which the second connection region is formed.

9. The connector as claimed in claim 8, wherein the first connection region has a connection section and the connection section is attached to the housing or to the second housing section, via the connection section in the second connection region and additionally comprising a sealing arranged between the connection section and housing for the purpose of sealing the connection section against the housing in liquid-tight fashion.

10. The connector as claimed in claim 8, wherein the first housing section and the second housing section are integral.

11. The connector as claimed in claim 7, further comprising a seal positioned between the connection and the housing for providing a liquid-tight seal of the connection against the housing.

12. The connector as claimed in claim 8, wherein the connection has a connection section and the connection is attached to the housing, optionally to the second housing section, via the connection section in the second connection region.

13. The connector as claimed in claim 11 wherein the seal is in the form of a sealing membrane.

14. The connector as claimed in claim 1, additionally comprising a second connection region for connecting a second container.

15. The connector as claimed in claim 14, wherein the first housing section and the piercing element are integral.

16. The connector as claimed in claim 14, wherein the second housing section and the piercing element are integral.

17. The connector as claimed in claim 1, wherein the connection area has an integral design.

18. The connector as claimed in claim 1, wherein the housing and/or the connection area are made of plastic.

19. The connector as claimed in claim 18, wherein the housing and/or the connection are made of polypropylene and/or of polycarbonate and/or of a blend and/or of a blend of polycarbonate and styrene-ethylene/butylene-styrene block copolymer.

20. The connector as claimed in claim 1, wherein the housing consists of a stiffer material compared to the connection area and the connection area consists of a more flexible material compared to the housing.

21. The connector as claimed in claim 1, wherein the first connection region is designed for connecting a glass flask or as a Luer connection.

22. The connector as claimed in claim 1, wherein the first connection region has a weld section for welding on a bag.

23. The connector of claim 1 wherein the connection area comprises a first angular range with a first wall bending strength and a second angular range with a second wall bending strength different than the first wall bending strength.

24. The connector of claim 23 wherein the first angular range defines a break-open region and the second angular range defines a hinge region.

25. The connector of claim 23 wherein the first angular range is greater than 180 degrees.

26. The connector of claim 23 wherein the first angular range is greater than 250 degrees.

27. The connector of claim 1, wherein as a result of a snapping movement of the break-open element, the connection area is detachable on a side facing away from the snapping movement and part of the connection area is able to remain on another side, forming a hinge for a further snapping movement.

28. The connector of claim 1, wherein the two stiffening webs are situated on the outside of the bending section.

29. The connector of claim 28 wherein the two stiffening webs extend in an axial direction and are positioned on the bending section to have a mirror symmetric design.

30. The connector of claim 1 wherein the two stiffening webs define only two snapping directions.

\* \* \* \* \*